US012584984B2

(12) United States Patent
Mostapha et al.

(10) Patent No.: US 12,584,984 B2
(45) Date of Patent: Mar. 24, 2026

(54) AI-POWERED HISTOLOGICAL FINGERPRINTING

(71) Applicant: Siemens Healthineers AG, Forchheim (DE)

(72) Inventors: Mahmoud Mostapha, Princeton, NJ (US); Dorin Comaniciu, Princeton, NJ (US); Mariappan S. Nadar, Plainsboro, NJ (US)

(73) Assignee: Siemens Healthineers AG, Forchheim (DE)

( * ) Notice: Subject to any disclaimer, the term of this patent is extended or adjusted under 35 U.S.C. 154(b) by 28 days.

(21) Appl. No.: 18/364,498

(22) Filed: Aug. 3, 2023

(65) Prior Publication Data

US 2025/0044390 A1      Feb. 6, 2025

(51) Int. Cl.
*G01R 33/56*      (2006.01)
*A61B 5/055*      (2006.01)

(52) U.S. Cl.
CPC .......... *G01R 33/5608* (2013.01); *A61B 5/055* (2013.01)

(58) Field of Classification Search
CPC ........................... A61B 5/055; G01R 33/5608
See application file for complete search history.

(56) References Cited

U.S. PATENT DOCUMENTS

| | | | | |
|---|---|---|---|---|
| 10,241,178 | B2 * | 3/2019 | Brady-Kalnay | ....... G01R 33/50 |
| 11,092,659 | B2 * | 8/2021 | Amthor | .............. G01R 33/4828 |
| 12,181,554 | B2 * | 12/2024 | Nezafat | .................. G01R 33/50 |
| 2022/0187405 | A1 * | 6/2022 | Wang | ..................... G16H 50/30 |
| 2022/0326328 | A1 * | 10/2022 | Hwang | ..................... G06T 5/60 |
| 2024/0361412 | A1 * | 10/2024 | Ma | ........................ G06T 11/005 |

OTHER PUBLICATIONS

C. Fan, Mapping the human connectome using diffusion MRI at 300 mT/m gradient strength: Methodological advances and scientific impact, NeuroImage 254 (2022), 118958. (Year: 2022).*
D. Heo, et al., Physics-based Decoding Improves Magnetic Resonance Fingerprinting, MICCAI 2023: 26th Inter. Conf., Proc., Part II, Oct. 8-12, 2023. https://doi.org/10.1007/978-3-031-43895-0_42. (Year: 2023).*
Huang, Susie Y., et al. "Connectome 2.0: Developing the next-generation ultra-high gradient strength human MRI scanner for bridging studies of the micro-, meso-and macro-connectome." Neuroimage 243 (2021): 118530.
Luo, Ziwei, et al. "Stochastic Actor-Executor-Critic for Image-to-Image Translation." arXiv preprint arXiv:2112.07403 (2021).
Sitzmann, Vincent, et al. "Implicit neural representations with periodic activation functions." Advances in Neural Information Processing Systems 33 (2020): 7462-7473.
Tendler, Benjamin C., et al. "The Digital Brain Bank, an open access platform for post-mortem imaging datasets." Elife 11 (2022): e73153.

* cited by examiner

*Primary Examiner* — Rodney E Fuller

(57)      ABSTRACT

Systems and methods for AI-powered histological fingerprinting in magnetic resonance imaging. MR signal data of an object is acquired using a high sensitivity scanner. Ground truth tissue microstructure data is acquired for the object. A forward model is learned using machine learning. The forward model is used to generate a dictionary or to train a model to map the signals to the histological parameters including the tissue microstructure of a scanner object. A signal-to-signal translation model is also provided to provide signals with improved sensitivity.

8 Claims, 6 Drawing Sheets

Magnetic Resonance Fingerprinting 150          Histological Fingerprinting 160

600

Simulated Signals with High Sensitivity
From Virtual Scanner (e.g., Connectome) 610

Signals with improved sensitivity
For histological fingerprinting
630

RL/DL Signal-to-Signal Translation 640

Low Sensitivity Signals from
current/low-cost scanners
620

AI-POWERED HISTOLOGICAL FINGERPRINTING

FIELD

This disclosure relates to medical image reconstruction, such as reconstruction in magnetic resonance (MR) imaging.

BACKGROUND

Medical imaging technologies, such as position emission tomography (PET), computed tomography (CT) and magnetic resonance imaging (MRI), have facilitated substantial advances in the diagnosis, monitoring, and treatment of disease. For example, Magnetic resonance imaging (MRI) is an important and useful imaging modality used in clinical practice. MRI is a non-invasive imaging technology that produces three dimensional detailed anatomical images. It is often used for disease detection, diagnosis, and treatment monitoring. Magnetic Resonance Fingerprinting (MRF) is an approach to quantitative MR imaging that allows simultaneous measurement of multiple tissue properties in a single, time-efficient acquisition. Quantitative MR imaging may provide data that may be used as imaging biomarkers for better characterization of tissue pathology, prognostication, follow-up, patient-specific management, and therapy design.

MRF is generally a three-step process including data acquisition, pattern matching and tissue property visualization. The data acquisition involves deliberately varying MR system settings and parameters, for example the MRF pulse-sequence, in a pseudorandom manner in order to generate unique signal evolutions, or fingerprints, for each combination of the tissue properties of interest. The fingerprints from individual voxels are compared with a collection of simulated fingerprints contained in a dictionary generated for that MRF sequence. The best match for the voxel fingerprint is selected from the dictionary through a pattern matching process. Once there is a pattern match, the combination of tissue properties that were used to generate the simulated fingerprint are identified as the underlying tissue properties in that voxel and these tissue properties are depicted as pixel-wise maps, thereby providing quantitative and anatomic information.

Despite MRF's recent success, MRF is still restricted to the conventional physics-based domain. In particular, for better adoption and effectiveness in clinical practice, quantitative images should describe biological phenomena and particularly histological properties of the tissue. The application of MRF to the histological properties of the tissue is hindered by disparate scales and resolutions between medical imaging and histology.

SUMMARY

By way of introduction, the preferred embodiments described below include methods, systems, instructions, and computer readable media for AI-powered histological fingerprinting in magnetic resonance imaging.

In a first aspect, a system for histological fingerprinting, the system comprising: an MRI scanner configured to generate signal evolutions for a sequence while scanning a patient; a histological forward model learned using machine learning, the histological forward model configured to input tissue microstructure properties and output signal evolutions; a histological dictionary created using the histological forward model; and an image processor configured to reconstruct an image including at least tissue microstructure properties of the patient, wherein the tissue microstructure properties of the patient are determined using the histological dictionary to map the signal evolutions to the tissue microstructure properties.

In a second aspect, a method for generating signals with improved sensitivity for histological fingerprinting, the method comprising: acquiring low sensitivity signal data of an object from a low sensitivity scanner; acquiring high sensitivity signal data of the object from a high sensitivity scanner; and training a model by inputting the low sensitivity signal data and the high sensitivity signal data into the model configured to generate realistic signal data with improved sensitivity when inputting data from the low sensitivity scanner.

In a third aspect, a method for learning a forward model for histological fingerprinting, the method comprising: generating electron microscopy of animal tissue; acquiring, by a high sensitivity MRI scanner, signals of the animal tissue; training a forward model using the electron microscopy and the signals of the animal tissue; and outputting a trained forward model for histological fingerprinting.

The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION

Figure 1:
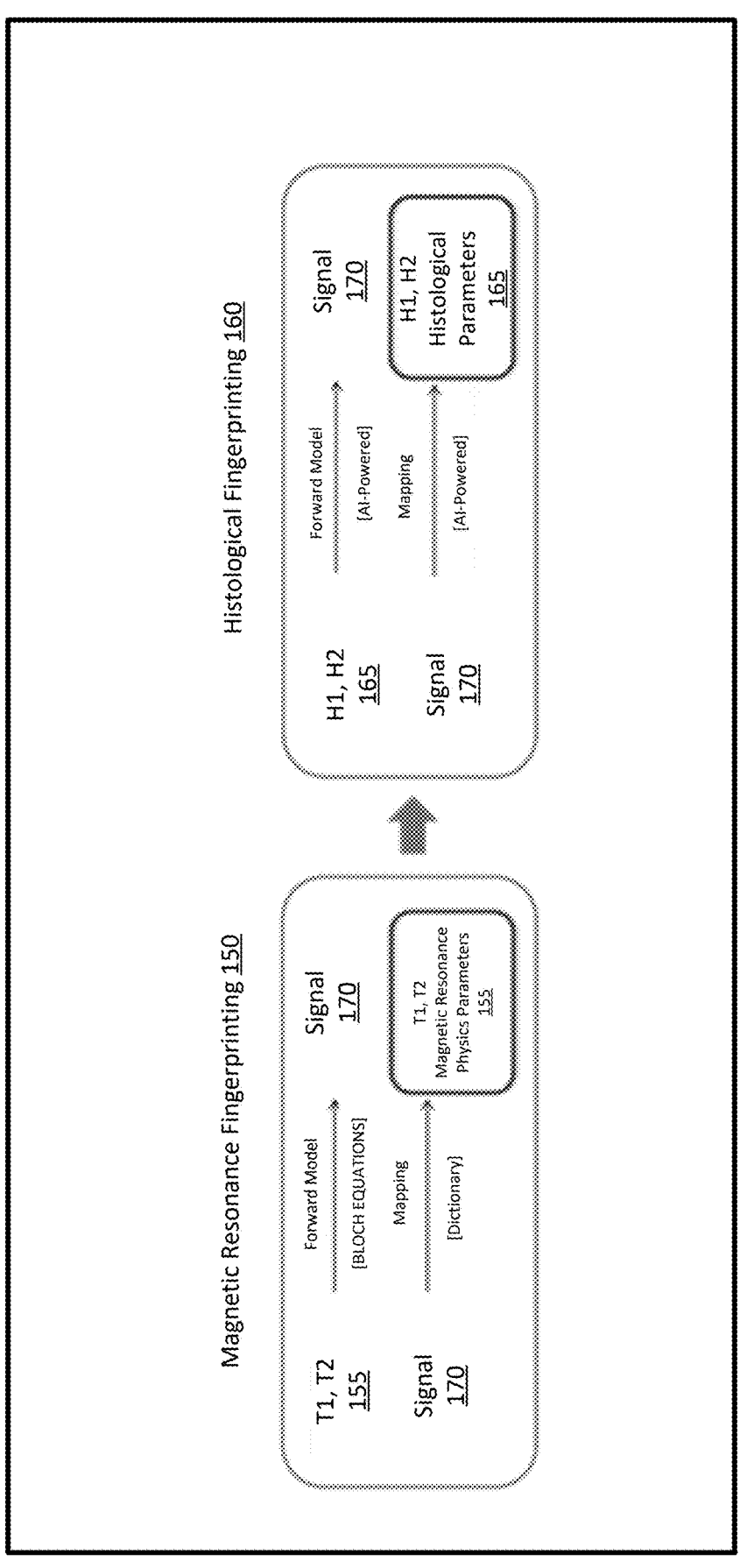
FIG. 1 depicts an example comparison between magnetic resonance fingerprinting and histological fingerprinting according to an embodiment.

Embodiments provide systems and methods for AI-powered histological fingerprinting in magnetic resonance imaging. MR signal data of an object is acquired using a high sensitivity scanner. Ground truth tissue microstructure data is acquired for the object. A forward model is learned using machine learning. The forward model is used to generate a dictionary or to train a model to map the signals to the histological parameters including the tissue microstructure of a scanner object. A signal-to-signal translation model is also provided to provide signals with improved sensitivity.

A key challenge in medical imaging is to understand how image properties correspond to specific elements of the tissue microstructure. In a conventional use, the side-by-side comparison with histologically stained tissue samples may be used as a validation for medical imaging. However, this comparison is challenged by substantial differences in scale and resolution between the two modalities. Imaging data is typically produced from 1-2 mm3 voxels in patients, compared to high-resolution (1-10 μm/pixel) but two-dimensional microscopy data, resulting in inherent limitations and inaccuracies in comparisons.

Magnetic Resonance Fingerprinting (MRF) is an approach to MRI that allows simultaneous measurement of multiple tissue properties in a single, time-efficient acquisition. Different physical phenomena, such as tissue proton relaxation times (T1, T2), are used as factors that influence the signal behavior. Bloch equations (also known as a forward model) may be used to calculate the signal for combinations of these properties. For quantitative imaging, a lookup table or a dictionary is constructed from the evolutions of such parameters. A matching or pattern recognition algorithm is then used to retrieve all the parameters used to build the signal. In MRF the acquisition parameters such as the radiofrequency excitation angle (FA) and phase, repetition time, and k-space sampling trajectory, are varied throughout the acquisition, that when implemented properly may generate a unique signal fingerprint for each tissue. Pattern matching involves matching the patterns of signal evolutions generated for individual tissue voxels, against the best corresponding entry in the overall dictionary of possible signal evolutions generated for that sequence. For every MRF sequence, the dictionary of signal evolutions may be generated on a computer using mathematical algorithms to predict spin behavior and signal evolution during that acquisition. Additional advances in MRF have been uncovered such as the use of machine learning for creating the dictionary and the matching, but the general concept remains in use.

Histology, also known as microscopic anatomy or microanatomy, is the branch of biology that studies the microscopic anatomy of biological tissues. Histology is the microscopic counterpart to gross anatomy, which looks at larger structures visible without a microscope. Although one may divide microscopic anatomy into organology, the study of organs, histology, the study of tissues, and cytology, the study of cells, modern usage places all of these topics under the field of histology. In particular as used herein, histology and histological properties/parameters refer to structural aspects of tissues that may not be discernible by conventional MRI or MRF.

One challenge with determining histological properties from MRI is the scale and resolution of conventionally acquired MRI data is not sufficient to derive histological properties of the scanned tissue. MR imaging data is typically produced from 1-2 mm3 voxels in patients, compared to high-resolution (1-10 μm/pixel) but two-dimensional microscopy data, resulting in inherent limitations and inaccuracies in comparisons. In an example, the size of an Axon radius is a potential biomarker for brain diseases and a crucial tissue microstructure parameter that determines the speed of action potentials. Axons are both structurally supportive of a neuron and the facilitators of communication. A cluster of axons together forms a nerve. The axonal membrane is a phospholipid bilayer that has proteins embedded inside it. These voltage-gated ion channels facilitate the movement of ions in and out of the membrane and are critical to the neuronal transmission. It would be very useful for diagnostic and other purposes to be able to quickly identify the microstructure of axons. However, most axons have a radius below one micrometer, which falls below the sensitivity limit of conventional MRI signals.

Conventional standard clinical scanners do not have enough sensitivity for many histological parameters (e.g., the inner diameter of axons). However, with recent advances in hardware and machine learning, new scanners may provide the sensitivity that is needed to start to pull out these histological parameters allowing MRF to move from the physics domain to the histological domain.

Embodiments described herein extend ideas from MRF to a new concept of histological fingerprinting where parameters such as H1, H2, etc. are described that correspond to histological parameters such as cell size, cell shape, cell wall permeability, etc. Histological fingerprinting is possible as individual differences in these cell properties are manifested by individual differences in the signals. FIG. 1 depicts an example of histological fingerprinting as compared to conventional MRF. In MRF 150, a forward model is used to determine signals 170 from tissue properties 155 (for example using Bloch equations). In histological fingerprinting 160 as described herein, a forward model is used to determine signals 170 from histological properties 165 (for example using an AI powered model). In MRF an acquired signal is mapped to the MR physics parameters using a dictionary generated using the forward model. In histological fingerprinting 160 the histological parameters/properties 165 are generated from MR signals 170 using an AI power model or a histological fingerprinting dictionary.

Embodiments provide an AI-powered framework to extend current MRF techniques to the histological level, enabling quantitative signals describing biological phenomena rather than the physics phenomena that MRF may provide. In addition, a virtual MRI scanner may be provided with a signal-to-signal translation that allows for achieving fast and realistic MRI simulations from low cost or low sensitivity scanners. With such data generation ability, the sensitivity of current scanners (or future low-cost scanners) may be improved with advancements in machine learning and gamification; for example, in an embodiment, a maximum entropy reinforcement learning framework is used to generate realistic signals from current scanners with the improved sensitivity required. With such approaches, embodiments may produce new signals that conventional applications haven't been able to access before.

Figure 2:
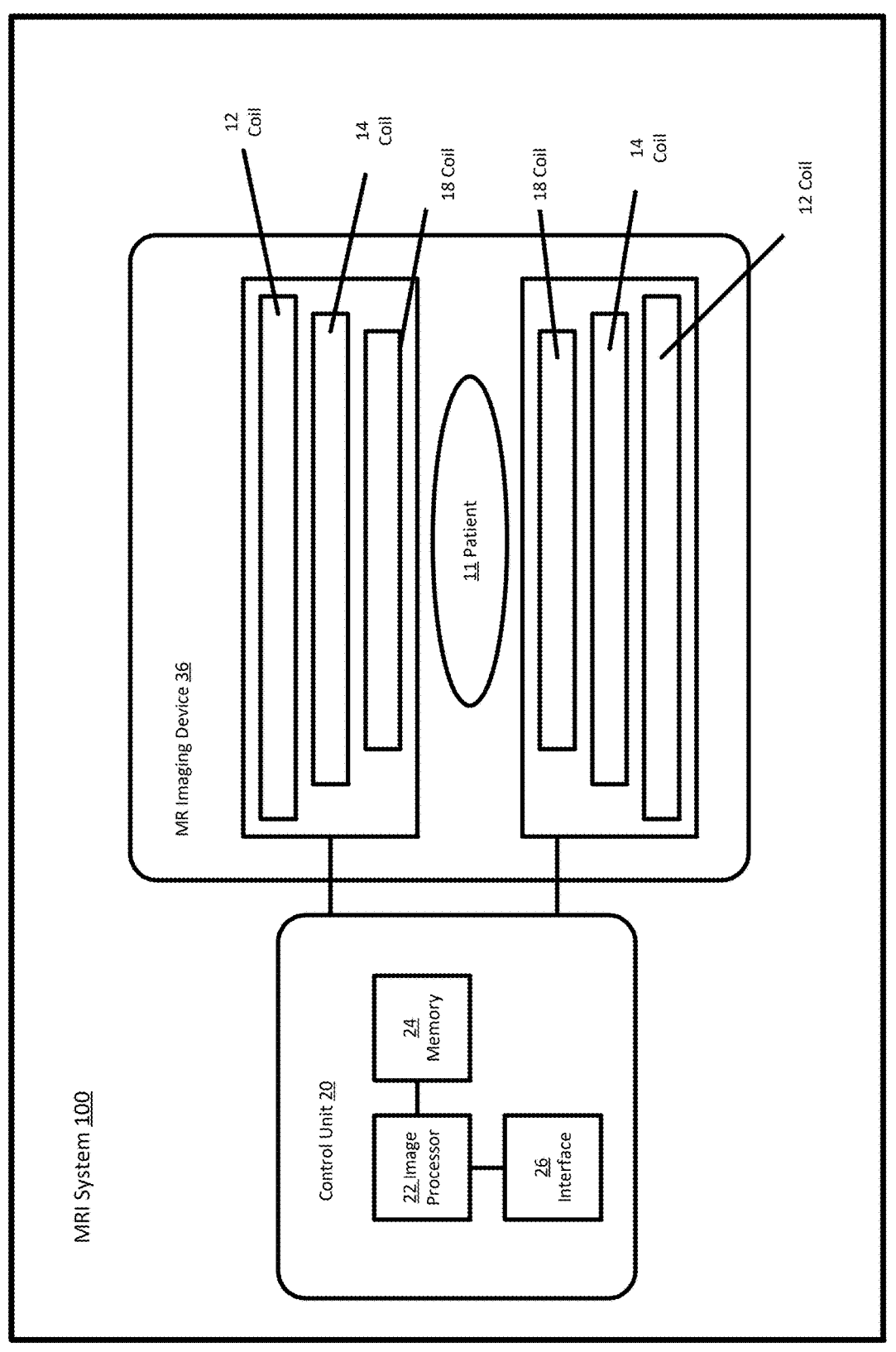
FIG. 2 depicts an example MRI system for histological fingerprinting according to an embodiment.

FIG. 2 depicts an embodiment of an MRI system 100 for AI-powered histological fingerprinting 160 in magnetic resonance imaging. The MRI system 100 is described below in general, with a following method providing other details. The MRI system 100 implements the method of FIGS. 3-6 or other instructions. The example used herein is in a MR context (i.e., a MR scanner), but other types of scanners may be used (e.g., reconstruction for CT, PET, SPECT, or other medical imaging). The MRI system 100 is implemented by an MR scanner, a computer based on data obtained by MR scanning, a server, or another processor. The MRI system 100 is only exemplary, and a variety of MR scanning systems may be used to collect the MR data. The MRI scanner 100 scans a patient to provide k-space measurements (measurements in the frequency domain).

In the MRI system 100, magnetic coils 12 create a static base magnetic field in the body of patient 11 to be positioned on a table and imaged. Within the magnet system are gradient coils 14 for producing position dependent magnetic field gradients superimposed on the static magnetic field. Gradient coils 14, in response to gradient signals supplied thereto by a gradient and shim coil control module, produce position dependent and shimmed magnetic field gradients in three orthogonal directions and generate magnetic field pulse sequences. A RF (radio frequency) module provides RF pulse signals to RF coil 18, which in response produces magnetic field pulses that rotate the spins of the protons in the imaged body of the patient 11 by ninety degrees, by one hundred and eighty degrees for so-called "spin echo" imaging, or by angles less than or equal to 90 degrees for so-called "gradient echo" imaging. Gradient and shim coil control module in conjunction with RF module, as directed by the control unit 20, control slice-selection, phase-encoding, readout gradient magnetic fields, radio frequency transmission, and magnetic resonance signal detection, to acquire magnetic resonance signals representing planar slices of patient 11.

In an embodiment, the gradient coils include a maximum gradient strength of 500 mT/m and slew rate of 600 T/m/s along each gradient axis. A maximum gradient amplitude of 300 mT/m may be considered a high sensitivity scanner. An asymmetric head gradient coil design may be used. The small inner diameter of the head gradient coil (compared to a conventional whole-body gradient coil) makes for a fundamentally efficient design enabling high maximum gradient strength per unit current. Additionally, the head gradient coil may include a substantially higher peripheral nerve stimulation (PNS) threshold compared to a typical whole-body gradient coil due to its smaller diameter, which increases the PNS threshold. In addition, the scanner may include a 72-channel head coil with an integrated field camera. This may provide improved reception sensitivity and dynamic field monitoring to enable distortion-reduced dMRI acquisitions. An example of this type of scanner is used in the Human Connectome Project which is mapping the macroscopic structural connections of the living human brain through the engineering of a whole-body human MRI scanner.

In response to applied RF pulse signals, the RF coil 18 receives MR signals, i.e., signals from the excited protons within the body as they return to an equilibrium position established by the static and gradient magnetic fields. The RF coil 18 may be a whole-body coil or may be formed from one or more local coils, at least on receive. The MR signals are detected and processed by a detector within the RF module and the control unit 20 to provide an MR dataset to an image processor 22 for processing into an image (i.e., for reconstruction in the object domain from the k-space data in the scan domain). In some embodiments, the image processor 22 is in or is the control unit 20. In other embodiments the image processor 22 is in a separate unit, for example, a cloud computing environment or computing system. An ECG synchronization signal generator may provide ECG signals used for pulse sequence and imaging synchronization. A two- or three-dimensional k-space storage array of individual data elements in k-space component processor unit stores corresponding individual frequency components forming an MR dataset. The k-space array of individual data elements may have a designated center, and individual data elements individually have a radius to the designated center.

The MRI system 100 is configured by the imaging protocol to scan a region of a patient 11 using different acquisition parameters. Instead of repeating the same acquisition parameters over time in a particular sequence until all the data in k-space have been obtained and used to reconstruct images with weighting by a particular property, in MRF the acquisition parameters such as the radiofrequency excitation angle (FA) and phase, repetition time, and k-space sampling trajectory, are varied throughout the acquisition, which when implemented properly may generate a unique fingerprint for each tissue. The magnetic field generator (comprising coils 12, 14 and 18) generates a magnetic field for use in acquiring multiple individual frequency components corresponding to individual data elements in the storage array. The imaging protocol for scanning a patient for a given examination or appointment may include different options, settings, or parameters that make up a protocol including, for example diffusion-weighted imaging (acquisition of multiple b-values, averages, and/or diffusion directions), turbo-spin-echo imaging (acquisition of multiple averages), or contrast. In an embodiment, the k-space is under sampled for more rapid scanning of the patient.

The control unit 20 uses information and algorithms stored in an internal database, for example stored in the memory 24, to process the detected MR signals in a coordinated manner to generate high quality images of a selected slice(s) of the body (e.g., using the image processor 22). The memory 24 may be or include an external storage device, RAM, ROM, database, and/or a local memory (e.g., solid state drive or hard drive). The same or different non-transitory computer readable media may be used for the instructions and other data. The memory 24 may be implemented using a database management system (DBMS) and residing on a memory 24, such as a hard disk, RAM, or removable media. Alternatively, the memory 24 is internal to the processor (e.g., cache). The stored information may for example include a forward model, fingerprint dictionary, and mapping algorithm/model. The data acquisition by the MRI system 100 involves deliberately varying the MR system settings and parameters, i.e. the MRF pulse-sequence, in a pseudorandom manner in order to generate unique signal evolutions, or fingerprints, for each combination of the tissue microstructure properties 165 of interest. The fingerprints from individual voxels are compared with a collection of simulated fingerprints contained in a dictionary generated for that MRF sequence. The best match for the voxel fingerprint is selected from the dictionary through a pattern matching process. The matching tissue microstructure/properties/parameters are used to generate an image or volume for display to an operator or further processing.

The MRI system 100 includes an operator interface 26, formed by an input and an output. The input may be an interface, such as interfacing with a computer network, memory, database, medical image storage, or other source of input data. The input may be a user input device, such as a mouse, trackpad, keyboard, roller ball, touch pad, touch screen, or another apparatus for receiving user input. Default, institution, facility, or group set levels may be input, such as from memory to the interface. The output is a display device but may be an interface. The final and/or intermediate images reconstructed from the scan are displayed. For example, an image of a region of the patient 11 is displayed. A generated image of the reconstructed representation for a given patient 11 is presented on a display of the operator interface 26. The display is a CRT, LCD, plasma, projector, printer, or other display device. The display is configured by loading an image to a display plane or buffer. The display is configured to display the reconstructed MR image of the region of the patient. The operator interface 26 may provide a graphical user interface (GUI) enabling user interaction with the control unit 20 and enables user modification in real time. The operator interface 26 may provide image representative data for display on a display device.

The control unit 20 (i.e., controller) includes a processor 22 that is an image processor 22 that reconstructs a representation of the patient from the k-space data. The image processor 22 is a general processor, digital signal processor, three-dimensional data processor, graphics processing unit, application specific integrated circuit, field programmable gate array, artificial intelligence processor, digital circuit, analog circuit, combinations thereof, or another now known or later developed device for reconstruction of an image from k-space data. The image processor 22 is a single device, a plurality of devices, or a network. For more than one device, parallel or sequential division of processing may be used. Different devices making up the image processor 22 may perform different functions, such as reconstructing by one device and volume rendering by another device. In one embodiment, the image processor 22 is a control processor or other processor of the MR scanner 100. Other image processors of the MR scanner 100 or external to the MR scanner 100 may be used. The image processor 22 is configured by software, firmware, and/or hardware to reconstruct. The instructions for implementing the processes, methods, and/or techniques discussed herein are provided on non-transitory computer-readable storage media or memories, such as a cache, buffer, RAM, removable media, hard drive, or other computer readable storage media, for example, the memory 24. The instructions are executable by the processor 22 or another processor. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the instructions set, storage media, processor or processing strategy and may be performed by software, hardware, integrated circuits, firmware, micro code, and the like, operating alone or in combination. In one embodiment, the instructions are stored on a removable media device for reading by local or remote systems. In other embodiments, the instructions are stored in a remote location for transfer through a computer network. In yet other embodiments, the instructions are stored within a given computer, CPU, GPU, or system. Because some of the constituent system components and method steps depicted in the accompanying figures may be implemented in software, the actual connections between the system components (or the process steps) may differ depending upon the manner in which the present embodiments are programmed.

In an embodiment, the control unit 20 of the MR imaging device 36 is configured to deliberately vary the MR acquisition settings, such as the radiofrequency excitation angle (FA) and phase, repetition time, and k-space sampling trajectory, i.e. the pulse-sequence, in a pseudorandom manner to generate unique signal evolutions, or fingerprints, for each combination of the properties of interest. The fingerprints are compared with a collection of simulated fingerprints contained in a histological dictionary generated for that sequence. The best match is selected from the histological dictionary through a pattern matching process. Once there is a pattern match, the combination of the tissue microstructure properties 165 that were used to generate the simulated fingerprint are identified as the underlying tissue microstructure properties 165 and these tissue microstructure properties 165 are depicted as pixel-wise maps. Conventional MRF may also be performed alongside histological MRF in order to provide additional information for the output representation. For example, the histological fingerprinting 160 may provide tissue structure while the conventional MRF may provide tissue types and other information.

The fingerprints may be determined using a forward model that maps each combination of the tissue microstructure properties 165 to the unique signal evolutions or fingerprints. The forward model is used to create a dictionary or train an AI model that then maps newly acquired signals to their respective tissue microstructure properties 165. The tissue microstructure properties 165 are then used to generate an image or representation. In an embodiment, a histological forward model is learned that maps the histology of the respective tissue to MR signals. The forward model is learned by using ground truth tissue microstructure data of a portion of tissue and using signals generated by a high sensitivity scanner that scanners the portion of the tissue. Implicitly defined, continuous, differentiable signal representations parameterized by neural networks may be used to learn the forward model first on animal tissue. In an example, electron microscopy of animal tissue is first generated and then the same animal tissue may be placed in an MRI scanner to generate a corresponding signal. Then AI techniques may be used to learn the forward model. Postmortem high-resolution MRI of human tissue with corresponding microscopy images may be also utilized if available, for example, platforms such as the Digital Brain Bank provide open access to curated, multimodal post-mortem neuroimaging datasets. In an embodiment, the learned forward model may be refined and customized for different clinical/low-cost scanners through RL/DL combined MRI simulations.

Figure 3:
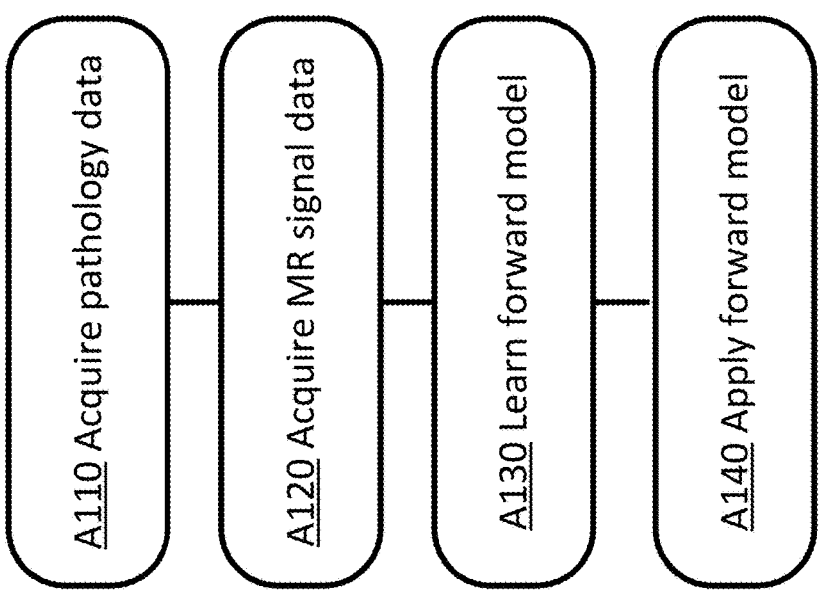
FIG. 3 depicts an example method for learning a forward model for histological fingerprinting according to an embodiment.

FIG. 3 depicts an example method for an AI-powered framework for learning a forward model from histology to an MR signal. The method is performed by the system 100 of FIG. 1, 2, 4, or 6 or another system. The method is performed in the order shown or other orders. Additional, different, or fewer acts may be provided.

At act A110, ground truth pathology data for a portion of tissue is acquired. In an embodiment, digital pathology is performed on a plurality of animal tissue and/or human postmortem tissue. In another embodiment, the ground truth pathology data may be acquired from a dataset or database that includes pathology data that was previously acquired. For digital pathology, electron microscopy may be used to determine the detailed structure of tissues, cells, organelles, and macromolecular complexes. In another embodiment, whole-slide images are used. Digital pathology is a subdiscipline of pathology focusing on generating, managing, and interpreting pathology information from digitized glass slides. One use of digital pathology is the digitization of glass slides into whole-slide scans. The components of the scanner parallel the ones of a microscope and include a light source, slide stage, objective lenses, and a high-resolution digital camera. An image may be acquired along the x/y-plane of the slide as a series of lines or tiles that are then digitally stitched together to create whole-slide images. Other methods of generating whole-slide scans may be used such as "Z-stacking" which is a method of scanning by which a series of images are captured at various focal planes, i.e., "slices," that are then combined to portray samples most effectively with 3D structures, such as clumps of cells or thick tissue. Whole-slide scans may use the Z-stack technique, e.g. extended depth of field or extended focus, which further enhances Z-stacking by combining the sharpest points of focus from each slice to maximize the depth of sharpness in the final image, demonstrated to be useful in cytology applications. The whole-slide images may be analyzed to determine/identify the microstructure properties of the tissue. Different methods may be used for analysis, including but not limited to segmentation, cell identification, AI approaches, etc. Object-based measurements, for example, rely on segmentation of the image into individual objects. These objects may be tissue structures composed of cells, as well as objects within tissue that are not comprised of cells. For objects composed of cells, the analysis approach may rely on first detecting cells and subsequently merging them into objects or detecting objects without performing prior cell segmentation. Once an object is identified, data may be extracted on an object-by-object basis. Based on the identification of individual cells and the segmentation of the tissue into these units, algorithms may then determine cellular structures such as cell size, diameter, cytoplasmic area, roundness, eccentricity, and nuclear orientation along the major axis among other properties. In AI-based approaches, the identification of different cellular and tissue features is based on providing the AI model with examples of different categories of structures and microstructures. The model learns to recognize the structures and microstructures and is subsequently able to detect and classify them in previously unseen images.

In an embodiment, data for human postmortem tissue may be acquired from an existing dataset such as the digital brain bank. The digital brain bank includes imaging data including submicron resolution microscopy to millimeter MRI acquisitions. The digital brain bank may provide both the MRI data (Act A120 below) and pathology data (Act A110). Further processing and analysis (such as labeling or annotating microstructure properties may be performed. The output of this step is a set of data that identifies the tissue microstructure properties 165 of particular animal tissue and/or human postmortem tissue.

At act A120, the plurality of animal tissue and/or human postmortem tissue is scanned using an MR scanner using one or more pulse sequences. In an embodiment, such as where human postmortem tissue is used, the MRI data may be preexisting and provided from a database that matches up with the digital pathology. As described above, current standard clinical scanners may not have enough sensitivity for many histological parameters (e.g., the inner diameter of axons). However, new scanners such as scanners used in the Connectome 2.0 project are many times more powerful as conventional systems, enabling imaging of human neuroanatomy with greater sensitivity than was previously possible. One example of such a high sensitivity scanner includes a maximum gradient strength of 300 mT/m and a slew rate of 200 T/m/s, with b-values tested up to 20,000 s/mm^2. For comparison, a standard gradient coil is 45 mT/m. Such high gradient strengths have benefited diffusion tractography by enhancing the resolution of complex fiber configurations for improved reconstruction of white matter fiber pathways. An important by-product of such dedicated high gradient systems is the unparalleled assessment of brain tissue microstructure in vivo through sensitizing the diffusion MRI signal to water diffusion within highly restricted compartments, thereby enabling the mapping of microstructural properties such as axon diameter, density, and g-ratio. Stronger scanners may also be used for example, an ultrastrong gradient human MRI scanner with even higher maximum amplitude of 500 mT/m is currently being developed. Similar to the MRF process, the high sensitivity MR scanner acquires data using varied acquisition parameters, for example different pulse sequences. The resulting signal evolutions or fingerprints are stored and compared to the ground truth data acquired in Act A110 to learn the forward model as described below in act A130 and generate a histological fingerprint dictionary or train a model.

In an embodiment, the MR data may be acquired using a low sensitivity scanner, for example a conventional MRI scanner. A signal-to-signal translation process may be used to input the low sensitivity signals from current scanners and output signals with improved sensitivity that may be used for histological fingerprinting 160. Simulated signals with high sensitivity from a virtual scanner or high sensitivity scanner may be used to train the signal-to-signal translation process using machine learning as described below in FIG. 4.

At act A130, a forward model is learned using the plurality of pathology data and MRI data as training data. Given a pseudo-random radio frequency (RF) pulse sequence, a distinct magnetic response—a.k.a. fingerprint, signature, or signal evolution—from each specific tissue is observed and then used to predict the target tissue properties. Multi-property quantification this is an inverse problem (of the forward model) that aims to infer underlying tissue properties from the magnetic responses. In an embodiment, the histological data from the pathology data is input and the AI model attempts to estimate the signal (from the MRI data). The results are compared with the ground truth and the AI model is adjusted. This process is repeated over and over until the AI model is able to solve the forward model and accurately estimate the signal.

Any trainable model may be used to learn the forward model. In an embodiment, the network is defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous and/or subsequent layer or unit. Skip connections may be used, such as a layer outputting to the sequentially next layer as well as other layers. Rather than pre-programming the features and trying to relate the features to attributes, the deep architecture is defined to learn the features at different levels of abstraction based on an input image data with or without pre-processing. The features are learned to reconstruct lower-level features (i.e., features at a more abstract or compressed level). For example, features for reconstructing an image are learned. For a next unit, features for reconstructing the features of the previous unit are learned, providing more abstraction. Each node of the unit represents a feature. Different units are provided for learning different features.

Various units or layers may be used, such as convolutional, pooling (e.g., max pooling), deconvolutional, fully connected, or other types of layers. Within a unit or layer, any number of nodes is provided. For example, one hundred nodes are provided. Later or subsequent units may have more, fewer, or the same number of nodes. In general, for convolution, subsequent units have more abstraction. For example, the first unit provides features from the image, such as one node or feature being a line found in the image. The next unit combines lines, so that one of the nodes is a corner. The next unit may combine features (e.g., the corner and length of lines) from a previous unit so that the node provides a shape indication. For transposed convolution to reconstruct, the level of abstraction reverses. Each unit or layer reduces the level of abstraction or compression. Different types or configurations may be used for the model or network.

Training is the process of inputting sample/training data into the model and receiving an output. The output is compared with an annotated expected output. Based on a loss function that describes the difference between the output and the expected output, the network is adjusted. This process is repeated hundreds, thousands, or more times until the output of the network reaches an acceptable level. The loss function is a measurement of how good the model is in terms of predicting the expected outcome. Different loss functions may be used during training and/or for testing the model. Two loss functions that may be used include cross-entropy and DICE. Cross-entropy is used to measure the difference between two probability distributions. It is used as a similarity metric to tell how close one distribution of random events is to another and is used for both classification (in the more general sense) as well as segmentation. DICE is used to calculate the similarity between images and is similar to the Intersection-over-Union heuristic. In an embodiment, a supervised encoder-decoder framework is used, where the encoder predicts the target tissue properties, and the decoder reconstructs the inputs. In another embodiment, a network (referred to as SIREN) leverages periodic activation functions for implicit neural representations.

Figure 4:
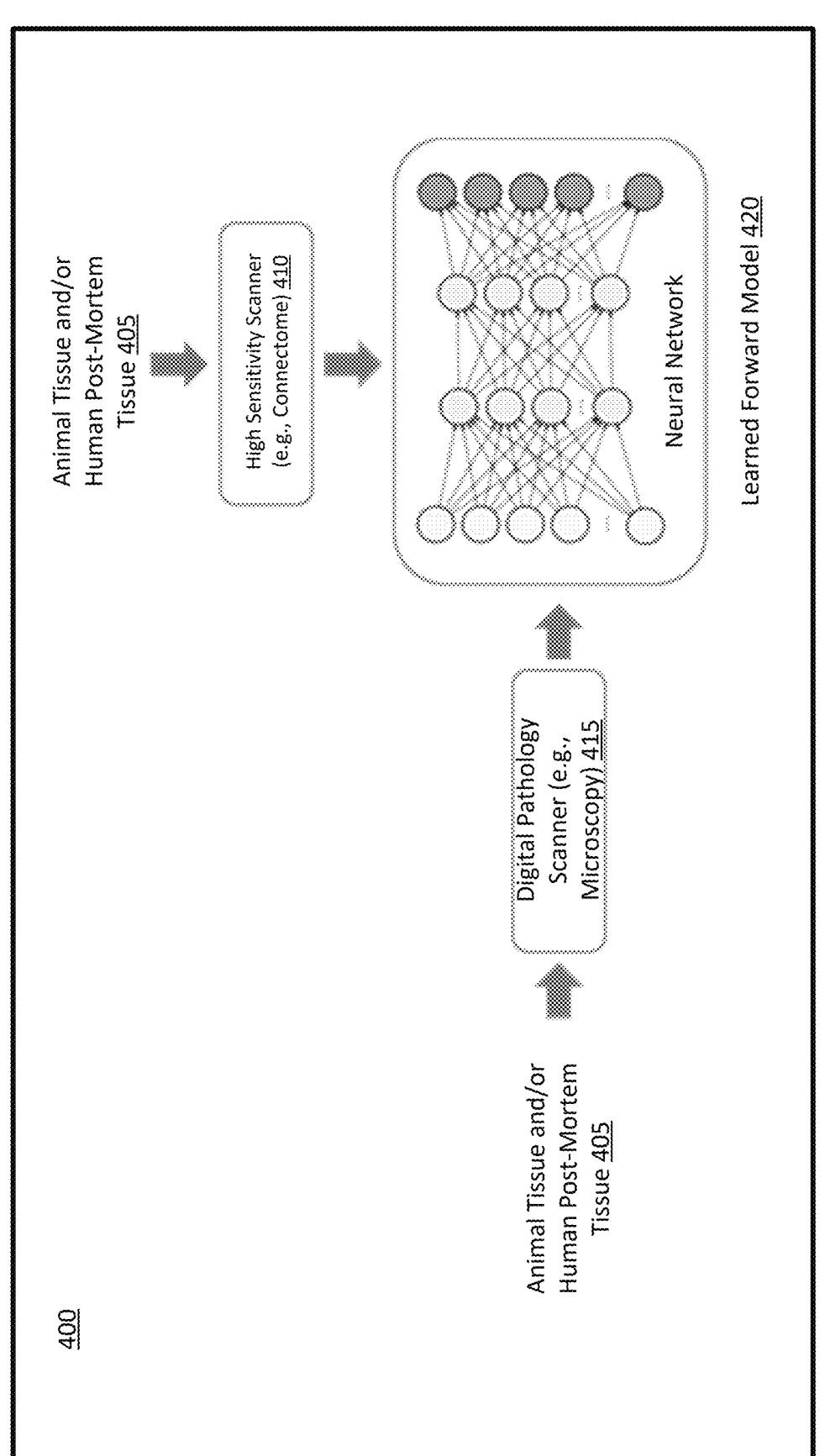
FIG. 4 depicts an example workflow for learning a forward model for histological fingerprinting according to an embodiment.

FIG. 4 depicts an example of learning a forward model 420. Animal Tissue and/or Human Post-Mortem Tissue 405 is input into a digital pathology scanner 415, for example that uses electron microscopy. The animal tissue and/or human post-mortem tissue 405 is also input into a high sensitivity scanner 410, for example as used in the connectome project. A neural network is trained on the output of the digital pathology scanner and the high sensitivity scanner to learn the forward model 420 for histological fingerprinting 160. Once the forward model 420 is learned, the signal may be mapped to the histological properties.

At act A140, the forward model is applied. The forward model may be used to generate a histological fingerprint dictionary that is used during a MR imaging session of a patient to determine the histology of a region of the patient. The forward model may also be used to train a model to map signals to histological properties. For a medical imaging procedure using MRF, once the magnetic responses are obtained, estimation of tissue microstructure properties 165 from responses reduces to a pattern recognition problem. In an embodiment, this may be addressed via dictionary matching (DM) which finds the best matching entry in a pre-computed dictionary for each inquiry magnetic response. Accordingly, the best matching dictionary entry leads to multiple tissue properties directly via a look-up-table (LUT) operation. More specifically, the pre-computed dictionary is composed of a number of magnetic responses for a variety of tissues microstructures characterized by the values of their intrinsic properties. In this way, each dictionary entry is associated with a specific tissue microstructure and its properties. Thus, once the best matching entry is found, it directly leads to multiple properties simultaneously through a LUT.

However, high computation and storage burden may make the DM-based approach prohibitively time-consuming and memory-consuming when the number of types and values of tissue properties increases, because the size of the dictionary and lookup table increases exponentially accordingly. Other model-based approaches may be used such as learning-based approaches by, for example, a trained neural network or model. To mimic the MRF processing, in an embodiment, the signals are input, and the tissue microstructure property values are estimated using a model or network trained using machine learning to perform the inverse of the forward model. The learned forward model may be used to train the model.

One requirement of the above-described process is the acquisition of high sensitivity MR data for both learning the forward model 420 and subsequent application of the histological fingerprints. In a clinical context, large, high-quality datasets may be difficult to obtain and expensive to generate. For example, the use of a high sensitivity MR scanner may be cost prohibitive or time consuming for an imaging procedure. Training the network on simulated dictionary data eliminates this concern and permits generating arbitrarily large training sets. Embodiments further provide a signal-to-signal translation framework for improving the sensitivity of signals from current/low-cost MRI scanners by jointly optimizing reinforcement learning and deep learning objectives. The signal-to-signal translation may be used by a virtual MRI scanner in order to output high sensitivity data.

Figure 5:
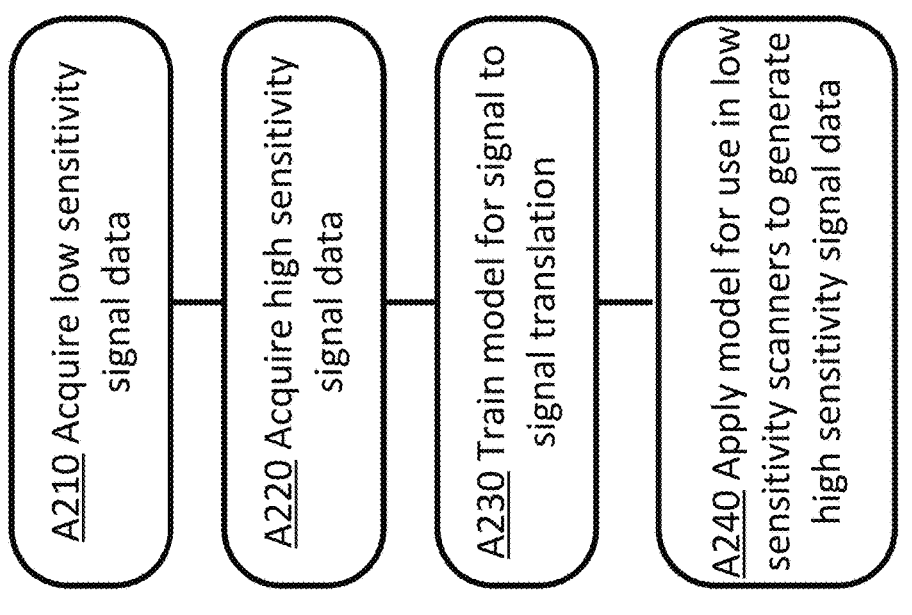
FIG. 5 depicts an example method for signal-to-signal translation for histological fingerprinting according to an embodiment.

FIG. 5 depicts a method for signal-to-signal translation that inputs low sensitivity signals from low sensitivity scanners and outputs signal with improved sensitivity that may be used with histological fingerprinting 160. The method is performed by the system 100 of FIG. 1, 2, 4, or 6 or another system. The method is performed in the order shown or other orders. Additional, different, or fewer acts may be provided.

At act A210, a plurality of low sensitivity signals are acquired from low sensitivity scanners of a patient. Any scanner may be used. The acquisition parameters such as the radiofrequency excitation angle (FA) and phase, repetition time, and k-space sampling trajectory, are varied throughout the acquisition, which when implemented properly may generate a unique signal fingerprint for each tissue microstructure.

At act A220, a plurality of high sensitivity signals are acquired from a high sensitivity scanner of the patient. In an embodiment, the high sensitivity signals may be acquired using a simulator. A high sensitivity signal simulator may be based on the learned forward model as described above. Low sensitivity signals may be matched with high sensitivity signals by using the forward model or inverse forward model.

At act A230, a model is trained to generate realistic signals from current scanners with improved sensitivity. The signal-to-signal translation may be similar to image-to-image translation. Image-to-image translation (I2IT) is often addressed by learning a generative process G that maps state x to target y, $G:x \rightarrow y$. The state should be consistent with the target and both of them are images. An autoencoder may be used to learn this process by minimizing the reconstruction error between the predicted image $\hat{y}$ and the target y.

In an embodiment, instead of directly mapping the input to the target image in a single step, a light-weight RL model may be used that performs the translation progressively, where new details may be added as the translation progresses. This model, referred to as stochastic actor-executor-critic (SAEC) includes three components: an actor, an executor, and a critic. Specifically, the actor and the executor form a DL pathway that directs the agent learning with a DL-based objective. The same actor and the critic form a deep reinforcement learning pathway that works as an actor-critic model. In the SAEC model, the actor generates a latent action according to a stochastic policy, so as to capture the required image translation control. The critic evaluates the stochastic policy. The executor leverages the latent action and image details to perform image translation and the generated image is then applied to the environment as the new input image at next time.

Figure 6:
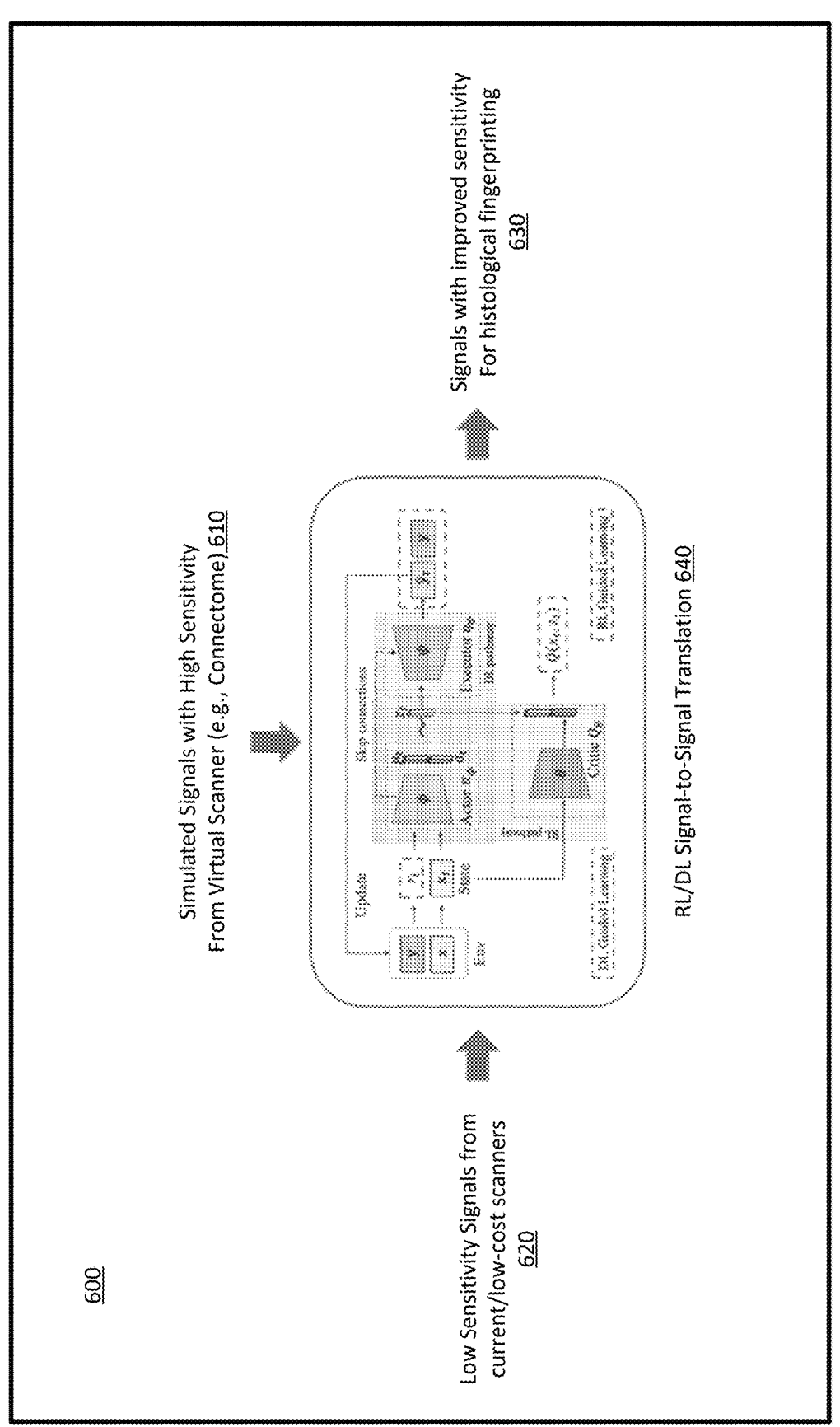
FIG. 6 depicts an example workflow for signal-to-signal translation for histological fingerprinting according to an embodiment.

FIG. 6 depicts an example workflow for generating realistic signals from current scanners with improved sensitivity. Low sensitivity signals are acquired from current/low-cost scanners 620. Simulated signals with high sensitivity are acquired from virtual scanners or high sensitivity scanners 610 to train a signal-to-signal model 640. The RL/DL signal to signal translation 640 outputs signals with improved sensitivity for histological fingerprinting 160. The signalto-signal model 640 may be used in a virtual MRI scanner to generate high sensitivity or improved sensitivity data.

In an embodiment, a generative network is used to perform the signal-to-signal translation. Alternative neural network configurations and training mechanisms may be used for the signal-to-signal network such as a convolution neural network (CNN), deep belief nets (DBN), or other deep networks. CNN learns feed-forward mapping functions while DBN learns a generative model of data. In addition, CNN uses shared weights for all local regions while DBN is a fully connected network (e.g., including different weights for all regions of a feature map. The training of CNN is entirely discriminative through backpropagation. DBN, on the other hand, employs the layer-wise unsupervised training (e.g., pre-training) followed by the discriminative refinement with backpropagation if necessary. In an embodiment, the arrangement of the trained network is a fully convolutional network (FCN). Alternative network arrangements may be used, for example, a three-dimensional Very Deep Convolutional Networks (3D-VGGNet). VGGNet stacks many layer blocks containing narrow convolutional layers followed by max pooling layers. A three-dimensional Deep Residual Networks (three-dimensional-ResNet) architecture may be used. A Resnet uses residual blocks and skip connections to learn residual mapping. Generative adversarial networks (GANs) may also be used.

Other models or machine learning techniques may be used. In an embodiment, a maximum entropy reinforcement learning (MERL) framework may be used. When using MERL, the agent tries to optimize the policy to choose the right action that may receive the highest sum of reward and long-term sum of entropy. This enables the agent to explore more and avoid converging to local optima. In an embodiment based on MERL, if there are a low number of probability distributions that would encode the prior data, then the best probability distribution is the one with maximum entropy. Thus, embodiments find the distribution that has maximum entropy. In many reinforcement learning algorithms, an agent may converge to local optima. In an embodiment, by adding the maximum entropy to the objective function, it enables the agent to search for the distribution that has maximum entropy. As the system has to search for the entropy as well, it enables more exploration and chances to avoid converging to local optima is higher.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description. Independent of the grammatical term usage, individuals with male, female or other gender identities are included within the term.

The following is a list of non-limiting illustrative embodiments disclosed herein:

Illustrative embodiment 1. A system for histological fingerprinting, the system comprising: an MRI scanner configured to generate signal evolutions for a sequence while scanning a patient; a histological forward model learned using machine learning, the histological forward model configured to input tissue microstructure properties and output signal evolutions; a histological dictionary created using the histological forward model; an image processor configured to reconstruct an image including at least tissue microstructure properties of the patient, wherein the tissue microstructure properties of the patient are determined using the histological dictionary to map the signal evolutions to the tissue microstructure properties.

Illustrative embodiment 2. The system of embodiment 1, wherein the MRI scanner includes a maximum gradient amplitude of 300 mT/m or more.

Illustrative embodiment 3. The system of one of the preceding embodiments, wherein the histological forward model is learned using an encoder decoder network.

Illustrative embodiment 4. The system of one of the preceding embodiments, wherein the histological forward model is learned using machine learning with post-mortem high-resolution MRI of human tissue with corresponding microscopy images.

Illustrative embodiment 5. The system of one of the preceding embodiments, wherein the histological forward model is learned using machine learning with tissue microstructure information acquired using digital pathology and respective signal data.

Illustrative embodiment 6. The system of embodiment 5, wherein the respective signal data is simulated.

Illustrative embodiment 7. The system of one of the preceding embodiments, wherein the tissue microstructure properties includes at least one of cell size, cell shape, or cell wall permeability.

Illustrative embodiment 8. The system of one of the preceding embodiments, further comprising: a display configured to display the image.

Illustrative embodiment 9. A method for generating signals with improved sensitivity for histological fingerprinting, the method comprising: acquiring low sensitivity signal data of an object from a low sensitivity scanner; acquiring high sensitivity signal data of the object from a high sensitivity scanner; and training a model by inputting the low sensitivity signal data and the high sensitivity signal data into the model configured to generate realistic signal data with improved sensitivity when inputting data from the low sensitivity scanner.

Illustrative embodiment 10. The method of one of the preceding embodiments, wherein the model is trained using a maximum entropy reinforcement learning framework.

Illustrative embodiment 11. The method of one of the preceding embodiments, wherein the high sensitivity signal data is simulated signal data.

Illustrative embodiment 12. The method of one of the preceding embodiments, wherein the model comprises a signal-to-signal model generated using both deep learning and reinforcement learning.

Illustrative embodiment 13. The method of one of the preceding embodiments, wherein the object comprises a specific cell structure.

Illustrative embodiment 14. A method for learning a forward model for histological fingerprinting, the method comprising: generating electron microscopy of animal tissue; acquiring, by a high sensitivity MRI scanner, signals of the animal tissue; training a forward model using the electron microscopy and the signals of the animal tissue; and outputting a trained forward model for histological fingerprinting.

Illustrative embodiment 15. The method of one of the preceding embodiments, further comprising: creating a histological dictionary using the trained forward model.

Illustrative embodiment 16. The method of embodiment 15, further comprising: applying the histological dictionary for image reconstruction during a medical imaging procedure.

Illustrative embodiment 17. The method of one of the preceding embodiments, wherein the forward model is trained using machine learning with post-mortem high-resolution MRI of human tissue with corresponding microscopy images.

Illustrative embodiment 18. The method of one of the preceding embodiments, wherein the forward model is trained using machine learning with tissue microstructure information acquired using digital pathology and respective signal data.

Illustrative embodiment 19. The method of one of the preceding embodiments, wherein the respective signal data is simulated.

Illustrative embodiment 20. The method of one of the preceding embodiments, wherein the high sensitivity MRI scanner includes a maximum gradient amplitude of 300 mT/m or more.

The invention claimed is:

1. A system for histological fingerprinting, the system comprising:

an MRI scanner configured to generate signal evolutions for a sequence while scanning a patient;

a histological forward model learned using machine learning, the histological forward model configured to input tissue microstructure properties and output signal evolutions;

a histological dictionary created using the histological forward model; and an image processor configured to reconstruct an image including at least tissue microstructure properties of the patient, wherein the tissue microstructure properties of the patient are determined using the histological dictionary to map the signal evolutions to the tissue microstructure properties.

2. The system of claim 1, wherein the MRI scanner includes a maximum gradient amplitude of 300 mT/m or more.

3. The system of claim 1, wherein the histological forward model is learned using an encoder decoder network.

4. The system of claim 1, wherein the histological forward model is learned using machine learning with post-mortem high-resolution MRI of human tissue with corresponding microscopy images.

5. The system of claim 1, wherein the histological forward model is learned using machine learning with tissue microstructure information acquired using digital pathology and respective signal data.

6. The system of claim 5, wherein the respective signal data is simulated.

7. The system of claim 1, wherein the tissue microstructure properties includes at least one of cell size, cell shape, or cell wall permeability.

8. The system of claim 1, further comprising:

a display configured to display the image.

* * * * *